(12) United States Patent
Ochi (10) Patent No.: US 8,701,676 B2
(45) Date of Patent: Apr. 22, 2014

(54) MAGNETIC CELL AND METHOD OF USING THE SAME

(75) Inventor: Mitsuo Ochi, Hiroshima (JP)

(73) Assignees: Eisai R&D Management Co. Ltd., Tokyo (JP); Mitsuo Ochi, Hiroshima (JP)

( * ) Notice: Subject to any disclaimer, the term of this patent is extended or adjusted under 35 U.S.C. 154(b) by 0 days.

(21) Appl. No.: 12/702,163

(22) Filed: Feb. 8, 2010

(65) Prior Publication Data

US 2010/0132722 A1   Jun. 3, 2010

Related U.S. Application Data (62) Division of application No. 10/554,259, filed as application No. PCT/JP2004/008972 on Jun. 25, 2004, now Pat. No. 7,971,592.

(30) Foreign Application Priority Data

Jun. 30, 2003   (JP) .................................. 2003-188626

(51) Int. Cl.
     *A61N 2/10*   (2006.01)
(52) U.S. Cl.
     USPC ........................................................ 128/899
(58) Field of Classification Search
     USPC ................. 128/899; 600/9–15; 435/174–182, 435/325–408, 366–372.3
     See application file for complete search history.

(56) References Cited

U.S. PATENT DOCUMENTS

| | | |
|---|---|---|
| 4,106,488 A | 8/1978 | Gordon |
| 4,219,411 A | 8/1980 | Yen et al. |
| 5,067,952 A | 11/1991 | Gudov et al. |
| 5,655,546 A * | 8/1997 | Halpern .................... 128/898 |
| 5,921,244 A * | 7/1999 | Chen et al. ................ 128/897 |
| 6,203,487 B1 | 3/2001 | Consigny |
| 7,971,592 B2 * | 7/2011 | Ochi ........................... 128/899 |

(Continued)

FOREIGN PATENT DOCUMENTS

| | | |
|---|---|---|
| JP | 05-228358 A | 9/1993 |
| JP | 06-133784 A | 5/1994 |

(Continued)

OTHER PUBLICATIONS

Stickel S, Wang Y. Synthetic Peptide GRGDS Induces Dissociation of Alpha-Actinin and Vinculin from the Sites of Focal Contacts. The Journal of Cell Biology 107: 1231-1239, Sep. 1988.*

(Continued)

*Primary Examiner* — Charles A Marmor, II
*Assistant Examiner* — Catherine E Burk
(74) *Attorney, Agent, or Firm* — Wolf, Greenfield & Sacks, P.C.

(57) ABSTRACT

In the present invention, because no examples are known of binding of magnetic particle to mesenchymal cell or chondrocyte which might be used in regenerative medicine, whether or not a cell having the magnetic particle bound thereto is retained in local by external magnetism after administration and whether or not the cell can exhibit intrinsic activity is studied. According to the present invention, a magnetic cell comprising mesenchymal cell or cultured chondrocyte having magnetic particle bound to the surface thereof is provided, and when the cell is administered in vivo and an external magnetic field is applied, the cell can be retained for a long time at a disease site. Moreover, a drug delivery system can be constructed by causing the magnetic cells to contain a drug.

6 Claims, 7 Drawing Sheets

(56) References Cited

U.S. PATENT DOCUMENTS

| | | | |
|---|---|---|---|
| 2002/0071843 A1 | 6/2002 | Li et al. | |
| 2003/0032995 A1* | 2/2003 | Handy et al. | 607/103 |
| 2003/0082148 A1* | 5/2003 | Ludwig et al. | 424/93.7 |
| 2005/0249731 A1* | 11/2005 | Aslan et al. | 424/144.1 |
| 2006/0264690 A1 | 11/2006 | Ochi | |

FOREIGN PATENT DOCUMENTS

| | | |
|---|---|---|
| JP | 11-092360 A | 4/1999 |
| WO | WO 00/71169 A2 | 11/2000 |
| WO | WO 00/71169 A3 | 11/2000 |
| WO | WO 02/30473 A1 | 4/2002 |

OTHER PUBLICATIONS

Kubo T, Sugita T, Shimose S, Nitta Y, Ikuta Y, Murakami T. Targeted delivery of anticancer drugs with intravenously administered magnetic liposomes in osteosarcoma-bearing hamsters. International Journal of Oncology 17: 309-315, 2000.*
Arbab et al., In Vivo Trafficking and Targeted Delivery of Magnetically Labeled Stem Cells. Human Gene Therapy. 2004;15:351-60.
Bates et al., Individual embryonic fibroblasts express multiple beta chains in association with the alpha v integrin subunit. Loss of beta 3 expression with cell confluence. J Biol Chem. Oct. 5, 1991;266(28):18593-9.
Elmi et al., A simple method for preparation of immuno-magnetic liposomes. Int. Journal of Pharmaceutics. 2001;215(1-2):45-50.
Jain et al., Magnetically Guided Rat Erythrocytes Bearing Isoniazid: Preparation, Characterization, and Evaluation. Drug Devl. and Ind. Pharm. 1997;23(10):999-1006.
Jansons et al., Targeted Liposomes: A Method for Preparation and Analysis. Analytical Biochemistry. 1981;111:54-59.
Kubo et al., Targeted delivery of anticancer drugs with intravenously administered magnetic liposomes in osteosarcoma-bearing hamsters. Int. J. Oncology. 2000;17(2):309-15.
Margolis et al., Magnetoliposomes: another principle of cell sorting. Biochimica et Biophysica Acta. 1983;735(1):193-95.
Matsunaga et al., Bio-separation by magnetic bead-based technology. Biomaterial. 2003 (February):113-19.
Nakamae et al., The Effect of an external magnetic force on cell adhesion and proliferation of magnetically labeled mesenchymal stem cells. Sports Med Arthtoscop Rehab Thera Technol. 2010;2(1):5. 8 pages.
Rucinski et al., Batroxostatin, an Arg-Gly-Asp-containing peptide from Bothrops atrox, is a potent inhibitor of platelet aggregation and cell interaction with fibronectin. Biochim Biophys Acta. Sep. 24, 1990;1054(3):257-62.
Stickel et al., Synthetic peptide GRGDS induces dissociation of alpha-actinin and vinculin from the sites of focal contacts. J Cell Biol. Sep. 1988;107(3):1231-9.
Sugita et al., Jiseitai Liposome o Mochiita Drug Delivery System ni Yoru Target Ryoho. Bio. Ind. 2002;19(6):47-53.
Swann et al., Differentiation-related changes in quantitative binding of immunomagnetic beads. Journal of Immunological Methods. 1992;152(2):245-51.
Yoshinori et al., Basic Study of cancer chemotherapy with maganetoliposomes containing CDDP. Japanese Oral Surgery Society. Feb. 1997:55-61.
Supplementary Partial European Search Report mailed Jun. 28, 2006 for corresponding EP App No. 04746441.7.
Extended European Search Report mailed Apr. 6, 2010 for corresponding EP App No. 09015815.5.
Extended European Search Report mailed Jul. 5, 2011 for corresponding EP App No. 10011721.7.
European Office Action mailed Apr. 5, 2007 for corresponding EP App No. 04746441.7.
Response to Apr. 5, 2007 Office Action filed Sep. 24, 2007 for corresponding EP App No. 04746441.7.
European Office Action mailed Apr. 2, 2009 for corresponding EP App No. 04746441.7.
Response to Apr. 2, 2009 Office Action filed Jul. 2, 2009 for corresponding EP App No. 04746441.7.
Summons to Attend Oral Proceedings for EP Publication No. 04746441.7 mailed Feb. 15, 2010.
Response to Feb. 15, 2010 Summons to Attend Oral Proceedings filed Apr. 15, 2010 for corresponding EP App No. 04746441.7.
Minutes of the Oral Proceedings for EP Publication No. 04746441.7 mailed Jun. 10, 2010.
European Office Action mailed Sep. 7, 2010 for corresponding EP App No. 09015815.5.
Response to Sep. 7, 2010 Office Action filed Nov. 11, 2010 for corresponding EP App No. 09015815.5.
European Office Action mailed Oct. 25, 2011 for corresponding EP App No. 10011721.7.
Response to Jul. 5, 2011 Extended Search Report filed Sep. 20, 2011 for corresponding EP App. No. 10011721.7.
Motoyama et al., In vitro cartilage formation using TGF-beta-immobilized magnetic beads and mesenchymal stem cell-magnetic bead complexes under magnetic field conditions. J Biomed Mater Res A. Jan. 2010;92(1):196-204.
Nakamae et al., The effect of an external magnetic force on cell adhesion and proliferation of magnetically labeled messenchymal stem cells. Sports Medicine, Arthroscopy, Rehabilitation, Therapy & Technology. 2010;2(1):1758-2555.
Office Communication mailed Jun. 21, 2013 for corresponding European App. No. 09015815.5.
Response to Dec. 12, 2011 Office Communication filed Mar. 6, 2012 for corresponding EP App No. 09015815.5.
International Preliminary Report on Patentability mailed Aug. 24, 2006 for corresponding App No. PCT/JP2004/008972.
Japanese Office Action mailed Jun. 5, 2006 for corresponding JP App No. 2005-511040.
Response to Jun. 5, 2006 Office Action filed Jul. 19, 2006 for corresponding JP App No. 2005-511040.
Japanese Office Action mailed Aug. 24, 2006 for corresponding JP App No. 2005-511040.
Response to Aug. 24, 2006 Office Action filed Sep. 12, 2006 for corresponding JP App No. 2005-511040.
Korean Office Action mailed Aug. 28, 2006 for corresponding KR App No. 10-2005-7010976.
Response to Aug. 28, 2006 Office Action filed Oct. 30, 2006 for corresponding KR App No. 10-2005-7010976.
Korean Office Action mailed Feb. 7, 2007 for corresponding KR App No. 10-2005-7010976.
Response to Feb. 7, 2007 Office Action filed Apr. 6, 2007 for corresponding KR App. No. 10-2005-7010976.
Notice of Allowance mailed Jun. 18, 2007 for corresponding KR App No. 10-2005-7010976.
Korean Office Action mailed Jun. 19, 2007 for corresponding KR App No. 10-2007-7007879.
Response to Jun. 19, 2007 Office Action filed Sep. 19, 2007 for corresponding KR App No. 10-2007-7007879.
Chinese Office Action mailed Jun. 29, 2007 for corresponding CN App No. 200480002945.1.
Response to Jun. 29, 2007 Office Action filed Oct. 29, 2007 for corresponding CN App No. 200480002945.1.
Notice of Allowance mailed Jan. 9, 2008 for corresponding KR App No. 10-2007-7007879.
Japanese Office Action mailed Jun. 20, 2008 for corresponding JP App No. 2006-196830.
Response to Jun. 20, 2008 Office Action filed Aug. 19, 2008 for corresponding JP App No. 2006-196830.
Office Communication mailed Apr. 15, 2009 for U.S. Appl. No. 10/554,259.
Response to Apr. 15, 2009 Office Action filed Sep. 15, 2009 for U.S. Appl. No. 10/544,259.
Chinese Office Action mailed Oct. 23, 2009 for corresponding CN App No. 200710167075.9.
Response to Oct. 23, 2009 Office Action filed Dec. 29, 2009 for corresponding CN App No. 200710167075.9.

(56) References Cited

OTHER PUBLICATIONS

Office Communication mailed Jan. 6, 2010 for U.S. Appl. No. 10/554,259.
Response to Jan. 6, 2010 Office Action filed Feb. 8, 2010 for U.S. Appl. No. 10/544,259.
Chinese Office Action mailed Feb. 24, 2010 for corresponding CN App No. 200710167075.9.
Response to Feb. 24, 2010 Office Action filed Apr. 20, 2010 for corresponding CN App No. 200710167075.9.
Office Communication mailed May 28, 2010 for U.S. Appl. No. 10/554,259.
Response to Jan. 6, 2010 Office Action filed Aug. 26, 2010 for U.S. Appl. No. 10/544,259.
Chinese Office Action mailed Jun. 23, 2010 for corresponding CN App No. 200710167075.9.
Response to Jun. 23, 2010 Office Action filed Aug. 24, 2010 for corresponding CN App No. 200710167075.9.
European Office Action mailed Dec. 12, 2011 for corresponding EP App No. 09015815.5.
Nierodzik et al., Role of platelets, thrombin, integrin IIb-IIIa, fibronectin and von Willebrand factor on tumor adhesion in vitro andmetastasis in vivo. Thromb Haemost. Jul. 1995;74(1):282-90.

* cited by examiner

|  | CD44 | | RGDS | |
|---|---|---|---|---|
| D | − | + | − | + |

Type II Collagen ← 448 bps
Aggrecan ← 322 bps
GAPDH ← 449 bps 35 cycle

MAGNETIC CELL AND METHOD OF USING THE SAME

RELATED APPLICATIONS

This application is a divisional application which claims the benefit under 35 U.S.C. §120 of U.S. application Ser. No. 10/554,259, entitled "MAGNETIC CELL AND METHOD OF USING THE SAME" filed on Oct. 25, 2005, now U.S. Pat. No. 7,971,592 which is a national stage filing under 35 U.S.C. §371 of PCT International application PCT/JP2004/008972, filed on Jun. 25, 2004, the contents of which are incorporated herein in their entirety.

TECHNICAL FIELD

The present invention relates to a magnetic cell which is useful for medicine, in particular for regenerative medicine, and to a method of using the same.

BACKGROUND OF THE DISCLOSURE

In general, a drug disperses throughout the body after administration, and it would be desirable for an anti-cancer agent and other drugs with strong side-effects to remain in high concentrations at the site of action without dispersing to other sites. A variety of efforts have been made to concentrate the drug locally. One method which has been attempted is to use a magnetic particle to concentrate the drug locally by means of a magnetic force exerted from outside the body. For example, it is possible to include a magnetic material together with the drug in liposome which is then administered and guided to a locality by the magnetic force, thus increasing the local concentration of the drug (see for example *Journal of the Japanese Oral Surgery Society*, February, 1997, pp. 55-61).

On the other hand, a technique is also known for modifying with an antibody the surface of a magnetic bead consisting of a polymer and a ferrimagnetic material such as magnetite and the like, and using an antigen-antibody reaction to isolate and produce a cell, and this technique has been applied to HLA typing, selection of hematopoietic stem cell and the like (see for example *Biomaterial*, February, 2003, pp. 113-119).

DETAILED DESCRIPTION OF THE DISCLOSURE

The Problems to be Solved by the Invention

However, there are no examples of binding of the magnetic particle to a mesenchymal cell, chondrocyte or other cells which might be used in regenerative medicine. Thus, many questions remain to be resolved, such as whether or not the cell having the magnetic particle bound thereto is retained locally by the external magnetic force after administration and whether or not the cell exhibits intrinsic activity.

Means for Solving the Problems

The inventors perfected the present invention as a result of exhaustive research focusing on the functions of the cell surface. That is, in a first aspect of the present invention, a magnetic cell is provided having a magnetic particle held on a surface of the cell. The composition of this cell allows it to be moved to a desired location using the magnetism of the magnetic particle.

In a preferred aspect of the magnetic cell according to the present invention, the surface and the magnetic particle are bound via a linker, or the surface is bonded via a specific amino acid sequence of the magnetic particle. Examples of the specific amino acid sequence include a peptide (RGDS) comprising the four amino acids, arginine-glycine-aspartic acid-serine and a peptide (GRGDS) comprising the five amino acids, glycine-arginine-glycine-aspartic acid-serine.

In a preferred aspect of the magnetic cell according to the present invention, the surface and the linker are bound by an antigen-antibody reaction.

In a preferred aspect of the magnetic cell according to the present invention, the linker and the magnetic particle are bound by a chemical bonding.

In a preferred aspect of the magnetic cell according to the present invention, the magnetic particle includes at least a magnetic material.

In a preferred aspect of the magnetic cell according to the present invention, the magnetic particle also includes a drug.

In a preferred aspect of the magnetic cell according to the present invention, the cell is selected from the group consisting of a cultured chondrocyte, a mesenchymal cell, a lymphocyte and a cell which expresses integrin.

In a second aspect of the present invention, a method for culturing the above magnetic cell is provided comprising preparing the magnetic cell and culturing the magnetic cell.

Moreover, in a third aspect of the present invention, a method for retaining the above magnetic cell is provided comprising moving the magnetic cell to a disease site in order to place the magnetic cell therein and retaining the magnetic cell at the disease site for a long time by means of a magnetic field.

In a preferred aspect of the retention method according to the present invention, the retaining step is accomplished either by applying the magnetic field to the disease site from outside the body or by embedding a magnet inside the body.

Moreover, in a fourth aspect of the present invention a method for controlling the activity of the above magnetic cell is provided comprising administering the magnetic cell and a magnetic particle comprising a drug to a disease site either simultaneously or separately, and releasing the drug from the magnetic particle.

In a preferred aspect of the control method according to the present invention, the drug is selected from the group consisting of a bone-forming agent, a cancer therapeutic agent and a dementia therapeutic agent.

Finally, in a fifth aspect of the present invention a treatment method is provided comprising administering the above magnetic cell and a magnetic particle comprising a drug to a disease site either simultaneously or separately, and releasing the drug from the magnetic particle.

In a preferred aspect of the treatment method according to the present invention, the drug is selected from the group consisting of a bone-forming agent, a cancer therapeutic agent and a dementia therapeutic agent.

Advantageous Effect of the Invention

Because with the magnetic cell according to the present invention the magnetic cell can be introduced into the body and kept for a long time at a disease site by an action of a magnetic field from outside the body, the intrinsic functions of the cell can be effectively expressed. Moreover, using the magnetic cell according to the present invention allows application to regenerative medicine including cartilage formation and to cancer drug and other drug delivery systems according to the necessity of therapy.

BEST MODE FOR CARRYING OUT THE INVENTION

The following embodiments are examples for explaining the invention, and the present invention is not limited to these embodiments. The present invention can be carried out in a variety of embodiments without departing from the spirit and scope of the invention.

First Embodiment

Figure 1:
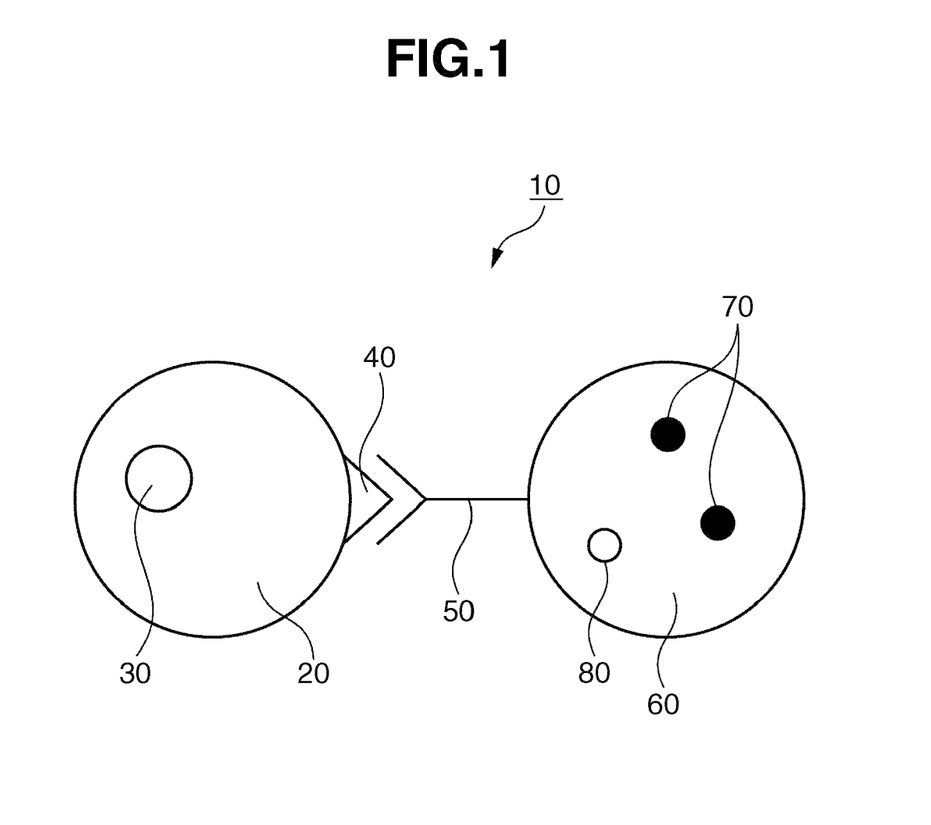
FIG. 1 shows a schematic view of the magnetic cell according to the first embodiment of the present invention.

The magnetic cell according to the present invention is based upon the use of an adhesive component on a surface of a cell. FIG. 1 shows a schematic view of a magnetic cell 10 of the first embodiment according to the present invention. This magnetic cell 10 comprises a magnetic particle 60, which is bound via a linker 50 to glycoprotein 40 expressed on the surface of the cell 20 having nucleus 30. Examples of the glycoprotein 40 used in the present invention include, but not limited to, CD44 or HLA.

Example of the magnetic particle 60 used in the present invention includes a liposome comprising a magnetic material 70. This liposome may also contain a drug 80, which can control cell activity, and the magnetic material and the drug may also be encapsulated using another type of capsule.

Here, the liposome is a spherical double lipid layer having an aqueous interior. When the liposome is formed, a molecule present in an aqueous solution is incorporated into the aqueous interior. The content incorporated into the liposome is protected from an external micro-environment and is efficiently transported inside the cytoplasm because the liposome fuses with the cell membrane.

Those commonly known as liposome can be used as the liposome used in the present invention, particularly those liposomes which can be used without problems for oral ingestion and injection. Such liposome can be used appropriately, or a liposome can be newly designed and formed using the known materials. More specifically, it is desirable to use a liposome which comprises phospholipids, ether glycerophospholipids, sphingophospholipids, glyceroglycolipids and sphingoglycolipids as the principal structural components of the liposome membrane, and which also comprises sterol, tocopherol and the like as lipid component which stabilize the liposome membrane.

Commonly known phospholipids can be used as the aforementioned phospholipids, including natural phospholipids, synthetic phospholipids and the like. Phospholipids which can be used favorably include (1) phosphatidylcholine, (2) phosphatidylethanolamine, (3) phosphatidylglycerol, (4) phosphatidylserine, (5) phosphatidic acid, (6) phosphatidylinositol and the like.

Examples of the aforementioned (1) phosphatidylcholine include egg yolk lecithin, soy lecithin, hydrogenated egg yolk lecithin, hydrogenated soy lecithin, soy-derived phosphatidylcholine, soy-derived hydrogenated phosphatidylcholine and other natural phosphatidylcholines; and synthetic systems such as phosphatidylcholine comprising a saturated or an unsaturated carboxylic acid with 7 to 22 carbon atoms. Specific examples include dimyristoyl phosphatidylcholine, dipalmitoyl phosphatidylcholine, dioleoyl phosphatidylcholine and the like. The fatty acid residues of the aforementioned may be octanoyl, nonanoyl, decanoyl, undecanoyl, lauroyl, myristoyl, palmitoyl, oleyl, stearyl, palmitoleyl, oleyl, linoleyl, linolenyl, arachidonyl or other groups. Moreover, the fatty acid residue parts which bind to the 1- and 2-sites of glycerin may be the same or different.

Examples of the aforementioned (2) phosphatidylethanolamine include soy-derived phosphatidylethanolamine, soy-derived hydrogenated phosphatidylethanolamine and other naturally phosphatidylethanolamines; and synthetic systems such as phosphatidylethanolamine comprising a saturated or an unsaturated carboxylic acid with 7 to 22 carbon atoms. Specific examples include dimyristoyl phosphatidylethanolamine, dipalmitoyl phosphatidylethanolamine, dioleoyl phosphatidylethanolamine and the like. The fatty acid residues may be groups such as those shown in (1) above.

Examples of the aforementioned (3) phosphatidylglycerol include such synthetic systems such as phosphatidylglycerol comprising a saturated or an unsaturated carboxylic acid with 7 to 22 carbon atoms. Specific examples include dimyristoyl phosphatidylglycerol, dipalmitoyl phosphatidylglycerol, dioleoyl phosphatidylglycerol and the like. The constituent fatty acid residues may be groups such as those shown in (1) above.

Examples of the aforementioned (4) phosphatidylserine include soy-derived phosphatidylserine, soy-derived hydrogenated phosphatidylserine and other natural systems; and synthetic systems such as phosphatidylserine comprising a saturated or an unsaturated carboxylic acid with 7 to 22 carbon atoms. Specific examples include dimyristol phosphatidylserine, dipalmitoyl phosphatidylserine, dioleoyl phosphatidylserine and the like. The constituent fatty acid residues may be groups such as those shown in (1) above.

Examples of the aforementioned (5) phosphatidic acids include synthetic acids such as phosphatidic acids comprising a saturated or an unsaturated carboxylic acid with 7 to 22 carbon atoms. Specific examples include dimyristol phosphatidic acid, dipalmitoyl posphatidic acid, dioleoyl phosphatidic acid and the like. The constituent fatty acid residues may be groups such as those shown in (1) above. Further, examples of the aforementioned (6) phosphatidylinositol include soy-derived phosphatidylinositol, soy-derived hydrogenated phosphatidylinositol and other natural systems, and synthetic phosphatidylinositol may also be used. The constituent fatty acid residues may be groups such as those shown in (1) above.

Glycerophospholipids, sphingophospholipids, glyceroglycolipids, sphingoglycolipids and the like can also be used as a membrane constituent of the liposome used in the present invention. In the present invention, sterols and tocopherols can be used as the lipid component to stabilize the liposome membrane. The aforementioned sterols may be those commonly known as sterols, and examples include cholesterol, sitosterol, campesterol, stigmasterol, brassicasterol and the like. Cholesterol is particularly desirable from the standpoint of availability and the like. The aforementioned tocopherols may be those commonly known as tocopherols, and for example commercial α-tocopherol is desirable from the standpoint of availability and the like.

The capsule material used in the present invention may be an ion-exchanged resin, crystalline ceramic, a biocompatible glass or latex. It may also be used as microsphere together with various surfactants. Moreover, nanosphere and other lipid, polymer or a protein material can be used as the aforementioned capsule material. The diameter of the capsule is not particularly limited but is preferably from tens to hundreds of nanometers. The drug capsule encapsulates at least a magnetic material and may either encapsulate or not encapsulate a drug, but it is desirable from the standpoint of cell control that the drug be encapsulated.

The drug capsule of the present invention may also be provided with a drug release control means for controlling drug release, and examples of drug release control means include a polymer, a temperature-sensitive molecule and an ultrasound- and/or a magnetism-sensitive substance. Specific examples include the polymer compound (polyacrylic acid polymer) with a clouding point described in Japanese Patent Application Laid-open No. H5-228358 and the ultrasound-sensitive substances (porphyrin derivative and xanthene derivative, etc.) described in Japanese Patent Application Laid-open No. 11-92360.

As long as the magnetic material is magnetic, there are no particular limits on the magnetic material used in the present invention, which may be paramagnetic, super-paramagnetic or ferromagnetic and the term "ferromagnetic" may include either ferromagnetic or ferrimagnetic. Specific examples of the magnetic material include magnetite ($Fe_2O_3$) and maghemite as well as compound particles of iron, cobalt, nickel and other ferromagnetic elements. Of these ferromagnetic materials, magnetite and maghemite are desirable because they exhibit no toxicity towards living bodies and are stable. Magnetite is particularly desirable.

The aforementioned magnetic material includes not only the aforementioned ferromagnetic compound particle by itself but also the magnetic particle which is embedded in cellulose, starch, dextran, agarose, methacrylate, styrene or the like, and the magnetic particle biosynthesized by a magnetic bacteria in which the magnetite is covered in phospholipids.

In the present invention, some method are explained whereby the surface of the aforementioned cell holds the magnetic particle. Such methods include a method in which reactive functional group of the cell surface is bound to reactive functional group of the magnetic particle by covalent bonding, and a method in which bonding is by means of a linker and the like. Examples of the linker used in the present invention include an antibody or compound (hereinafter, "bifunctional spacers") having a carboxyl group, an amino group or other reactive functional groups at both ends. Preferred examples of the method of binding the linker to cell magnetic bacteria include a method of binding the reactive functional group on the cell surface via the bifunctional spacer to the magnetic particle covered with a phospholipid film which is obtained by crushing the magnetic bacteria, and a method of binding HLA, CD44 or other adhesive molecules on the cell surface via an antigen-antibody reaction to an antibody used as a linker which is bound via an amide bond to the magnetic particle the surface of which have been modified with the carboxyl group.

In the magnetic cell used in the present invention the magnetic particle may be included within the cell, or may be bound to the cell surface, or may be bound to the cell surface via a linker. A magnetic particle may be included within the cell, for example, by a method using a particle gun as described in Japanese Patent Application Laid-open No. H6-133784.

In the first embodiment of the present invention, the drug 80 which is contained in the aforementioned magnetic particle 60 may be a bioactive substance such as a cytokine or other substance which governs the cell signal transmission system, although it is not limited to these. Specific examples of cytokines include interferons (IFN-α, IFN-β, IFN-γ and the like), interleukins (IL-1 through IL18 and the like), lymphotoxins, tumor necrosis factors (TNFα and the like) granulocyte-macrophage colony stimulating factor (GM-CSF), macrophage colony stimulating factors (M-CSF, CSF-1), granulocyte colony stimulating factor (G-CSF), erythropoietin, thrombopoietin, hematopoietic stem cell factor (SCF), monocyte chemotactic activity factor (MCAF), transforming growth factors (TGF-α, TGF-β), fibroblast growth factor (FGF), epithelial growth factor (EGF), platelet-derived growth factor (PDGF), nerve growth factor (NGF) and the like. In particular, interferons, interleukins, tumor necrosis factors, erythropoietin, thrombopoietin, transforming growth factors, fibroblast growth factor, epithelial growth factor, platelet-derived growth factor and nerve growth factor are preferred.

The aforementioned drug 80 may be a drug for a disease to be prevented and/or treated at the disease site. Although not limited thereby, specific examples of drugs include an anti-cancer drug such as irinotecan hydrochloride trihydrate, mitomycin C, 5-fluorouracyl, cisplatin, gemcitabine hydrochloride, doxorubicin, taxol and the like. Other examples include donepazil and other Alzheimer drugs. The magnetic cell according to the present invention can be used as a drug delivery system by incorporating this drug 80 into the liposome part of the magnetic cell.

The aforementioned drug 80 may form a salt. Favorable examples of this salt include salts of inorganic acids, salts of organic acids, salts of inorganic bases, salts of organic bases, and salts with acidic or basic amino acids. Of these, pharmacologically acceptable salts are preferred. Favorable examples of salts with inorganic acids include salts with hydrochloric acid, hydrobromic acid, sulfuric acid, nitric acid, phosphoric acid and the like, while favorable examples of salts with organic acids include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid and the like. Favorable examples of salts with inorganic bases include sodium salts, potassium salts and other alkaline metal salts, calcium salts, magnesium salts and other alkaline earth metal salts, and aluminum salts, ammonium salts and the like. Favorable examples of salts with organic bases include salts with diethylamine, diethanolamine, meglumine, N,N'-dibenzylethylenediamine and the like.

When the aforementioned drug 80 is administered to the patient as a preventative or therapeutic drug for an associated disease, there are no limits on the administration route, dosage or number of administrations, which vary depending on the patient's symptoms, type and severity of the disease, age, heart, liver and kidney functions and the like. For example, in the case of therapy for cancer in a human, 0.01 mg to 1000 mg or preferably 0.1 mg to 1000 mg or more preferably 0.1 mg to 100 mg can be administered daily to an adult in the case of oral administration, and 0.01 mg to 500 mg or preferably 0.1 mg to 500 mg or more preferably 0.1 mg to 100 mg daily to an adult in the case of intravenous administration, divided into 1 to 5 administrations per day depending on the symptoms.

A drug composition comprising the aforementioned drug 80 can also be introduced into the magnetic cell, and the aforementioned composition can be manufactured by a known method using excipients, lubricants, binders, disintegrators, stabilizers, flavorings, diluents and other additives. Specific examples of excipients include organic excipients such as lactose, saccharose, glucose, corn starch, potato starch, alpha starch dextrin and other starch derivatives, crystal cellulose and other cellulose derivatives, gum arabic, dextrin, and pullulan; and inorganic excipients such as light silicic anhydride, synthetic aluminum silicate, calcium silicate, magnesium metasilicate aluminate and other silicate derivatives, calcium hydrogenphosphate and other phosphate derivatives, calcium carbonate and other carbonates, calcium sulfate and other sulfates and the like. Specific examples of lubricants include stearic acid, stearic acid metal salts such as calcium stearate and magnesium stearate, talc, colloidal silica, waxes such as bee gum and spermaceti, boric acid, adipic acid, sulfates such as sodium sulfate, glycol, fumaric acid, sodium benzoate, DL-leucine, fatty acid sodium salts, lauryl sulfates such as sodium lauryl sulfate and magnesium lauryl sulfate, silicic acids such as silicic anhydride and silicic hydrate, and the aforementioned starch derivatives. Specific examples of binders include hydroxypropyl cellulose, hydroxypropyl methylcellulose, polyvinylpyrrolidone, macrogol, and compounds such as the aforementioned excipients. Specific examples of disintegrators include cellulose derivatives such as low-substitution hydroxypropylcellulose, carboxymethylcellulose, carboxymethylcellulose calcium, and internally cross-linked carboxymethylcellulose sodium as well as carboxymethyl starch, carboxymethyl starch sodium, cross-linked polyvinylpyrrolidone and other chemically modified starches, cellulose and the like. Specific examples of stabilizers include paraoxybenzoic acid esters such as methylparaben and propylparaben, alcohols such as chlorobutanol, benzyl alcohol and phenylethyl alcohol, benzalkonium chloride, phenols such as phenol and cresol, thimerosal, dihydroacetic acid, and sorbic acid and the like. Specific examples of flavorings include sweeteners, acid flavors, aromatics and the like which are commonly used in preparations.

Although not limited thereby, the cell used in the present invention is preferably lymphocyte, mesenchymal stem cell, cultured chondrocyte or the like.

Second Embodiment

Figure 2:
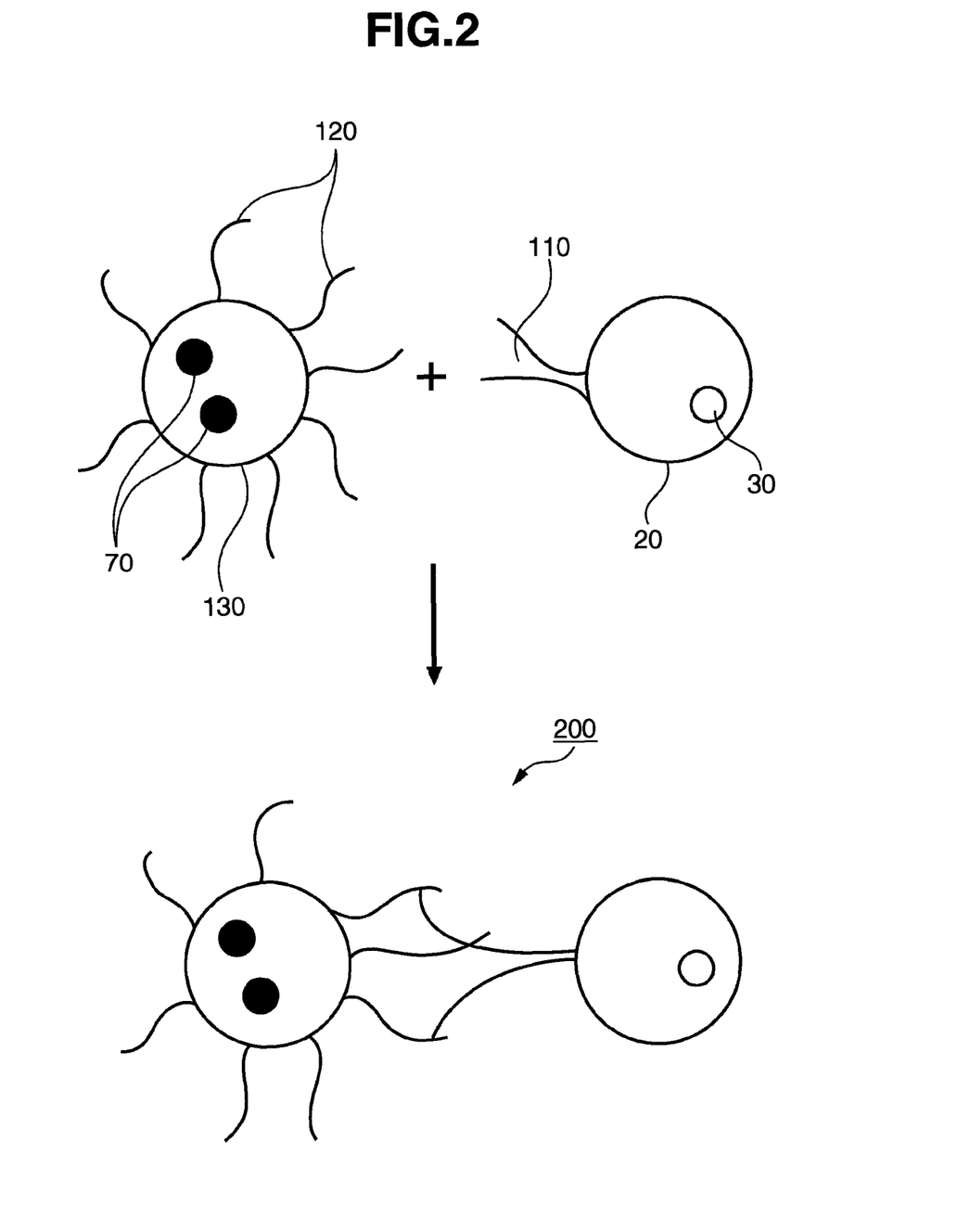
FIG. 2 shows a schematic view of the magnetic cell according to the second embodiment of the present invention.

FIG. 2 shows a schematic view of a magnetic cell according to the second embodiment of the present invention. The second embodiment of the present invention uses integrin 110 present on the cell surface and peptide 120, which has adhesive activity with respect to integrin. Although not limited thereby, the aforementioned peptide may be RGDS (a peptide consisting of the four amino acids arginine-glycine-aspartic acid-serine, molecular weight 433.42).

In the second embodiment of the present invention, the magnetic cell 200 having a magnetic particle on the surface is provided through the use of activated magnetic bead 130, which is modified with the amino acid sequence of RGDS on the surface of the magnetic bead.

This magnetic cell can be prepared as follows. First, a magnetic bead the surface of which has been modified in advance with a carboxyl group is activated by means of a reagent. The reagent for activation is not particularly limited as long as it can activate the carboxyl group, but a carbodiimide is preferred. Second, the activated carboxyl group on the surface of the magnetic bead and the amino group of the peptide are reacted to form amide bond, introducing the peptide onto the surface of the magnetic bead.

In the present invention, the amount of the peptide coated on the bead may be 10 ng to 20 µg of antibody or peptide which forms a ligand per 3 mg equivalent of magnetic bead, and is preferably 15 ng to 15 µg or more preferably 20 ng to 10 µg. That is, in terms of unit weight of magnetic bead, 3 ng to 6.6 µg can be coated per 1 mg of magnetic bead. If too much peptide is coated on the magnetic bead, the final magnetic cells end up adhering to each other, impeding movement to the disease site which is the target. If too little is coated, the properties of the magnetic cell itself cannot be achieved.

Next, the magnetic bead with introduced peptide and the adhesion molecule on the target cell surface are reacted to prepare the magnetic bead according to the present invention. For purposes of the reaction the amount of peptide-introduced magnetic bead depends on the percentage of peptide introduction, but is preferably 0.1 µl to 20 µl or more preferably 0.2 µl to 18 µl or still more preferably 0.5 µl to 15 µl per $2 \times 10^5$ of the aforementioned target cells. If the amount of peptide-introduced magnetic bead is 0.1 µl or less, the magnetic cell itself will not perform function, while if the amount of peptide-introduced magnetic bead is 20 µl or more, the magnetic cells will adhere to one another, impeding movement to the disease site which is the target.

Although not limited thereby, the reaction solution for reacting the peptide-introduced magnetic bead with the adhesion molecule on the cell surface may be BSA (bovine serum albumin) phosphate buffered saline (hereunder, "BSA/PBS"), and a solution of BSA/PBS with EDTA (ethylenediaminetetraacetic acid) added, 0.5% BSA 4.4 µM EDTA in PBS (−) (EDTA concentration 4.4 µM to 2 mM) is preferred.

In the second embodiment of the present invention, a person skilled in the art could easily understand that the magnetic material and the drug in the first embodiment can be used in the same way.

Next, the method of using the magnetic cell according to the present invention will be explained. The magnetic cell prepared as described above can be used in therapy as described below if cultured in a variety of cells. The culture fluid and temperature in the culture can be selected as appropriate. The culture fluid depends on the cells used, but for example a culture fluid based on DMEM (Dulbecco's modified Eagle's medium) is suitable in the case of cultured chondrocytes.

The magnetic cell according to the present invention can be used in therapy by being retained for a long time at a target disease site according to the type of cells. For example, using myeloid mesenchymal stem cell chondroid tissue can be formed at a disease site. Consequently, it is important that the magnetic cell according to the present invention be retained for a long time at the target disease site.

The term "retained for a long time at a disease site" used in the present invention means that the magnetic cell is retained long enough for its functions to be performed, and a period of 1 to 90 days or preferably 1 to 80 days or more preferably 1 to 50 days is desirable. The site of administration of the magnetic cell according to the present invention may be a site with a lesion in the body or a site subjected to treatment, and examples include the brain, bone, liver, heart, joints and the like. Specific examples of diseases include cerebral hemorrhage, malignant tumors, spinal cord damage, cartilage defects, muscle defects, ligament damage and the like.

Administration of the magnetic cell according the present invention for retention inside the body may be by surgical methods or by injection. Surgical administration means administration by opening a hole in a bone for example, while injection means direct administration by injection to a disease site or general administration by intravenous injection.

The term "magnetic field" used in the present invention preferably means a field of 60 gauss (hereinafter "G") or more for purposes of magnetizing the magnetic particle, and 70 G or more is preferred for purposes of retaining the particle in a specific location and preventing dispersion within the body. The magnetic field can be applied from outside the body or can be applied by embedding a magnet in the body. In this case, a neodymium magnet is preferred from the standpoint of magnetic force of the magnet, stability and strength.

Figure 3:
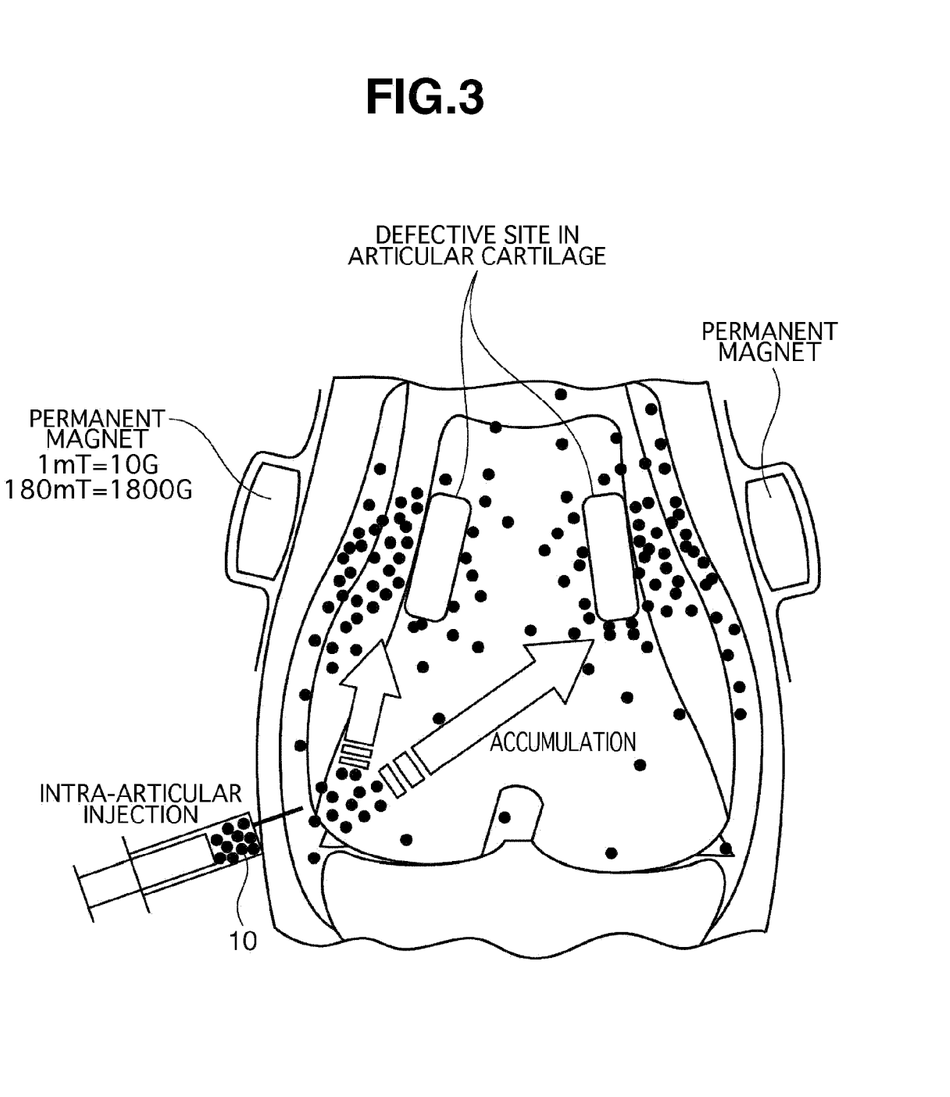
FIG. 3 is a drawing explaining the recovery of cartilage as regenerative medicine.

FIG. 3 shows a schematic view of therapy using the magnetic cell according to the present invention. As shown in FIG. 3, the magnetic cell according to the present invention is introduced in vivo by intra-articular injection. Because the permanent magnet is arranged at the location where the magnetic cell is to be moved and placed, the magnetic cell according to the present invention can be moved to the desired location by the action of the magnetic force of the aforementioned permanent magnets. In FIG. 3, the magnetic cell can be moved to a defective site in articular cartilage and placed there. If a cell used as the magnetic cell according to the present invention is myeloid mesenchymal stem cell, it is possible to form chondroid tissue on site and repair the aforementioned defective site.

Cartilage repair, which is a research attention of the regenerative medicine, was explained in FIG. 3, but if the location of treatment is a cancer cell, it is possible to locally concentrate a drug by including an anti-cancer drug in the magnetic particle which makes up the magnetic cell.

Drug release from magnetic cell according to the present invention which has been administered in vivo is controlled by means of enzyme or other action, temperature or the like.

The term "controlling the activity of magnetic cell" used in the present invention means the controlling cell activity such as differentiation or proliferation by means of cytokines or other drugs.

The magnetic cell and drug capsule may be administered either simultaneously or separately, and for example one mode would be a drug kit in which the magnetic cell and drug capsule are included as injections in a single package.

INDUSTRIAL APPLICABILITY

With the magnetic cells according to the present invention, because the magnetic cells can be introduced in vivo and retained for a long time in a disease site by the action of an externally applied magnetic field, the intrinsic functions of the cells can be effectively expressed. Moreover, the magnetic cells according to the present invention can be applied to chondrogenesis and other regenerative medicine and as drug delivery systems for the anti-cancer drug and the like depending on the need for therapy.

The present invention is explained in more detail using the following examples, but the scope of the present invention is not limited thereby. Various changes and modifications by the persons skilled in the art are possible based on the descriptions of the present invention, and these changes and modifications are included in the present invention.

EXAMPLES

Preparation of Magnetic Cell 1

1. Activation of Magnetic Beads 3 mg equivalent (60 µl) was taken from a ferrisphere 100C stock solution (manufactured by Japan Paint; 50 mg/ml) as the magnetic beads, and washed by adding 0.01 N NaOH and stirring at room temperature for 10 minutes in a mixer. This washing operation was repeated once, and washing was performed again by adding de-ionized water and stirring at room temperature for 5 minutes in the mixer. This washing operation was repeated 3 times. To activate the magnetic beads, excess water was removed and the magnetic beads were mixed thoroughly in a tube with 50 µl each of 1-ethyl-3-(3-dimethylaminopropyl)carbodiimide hydrochloride (hereinafter "EDC", manufactured by Sigma) and N-hydroxysuccinimide (hereinafter "NHS", manufactured by Sigma) pre-prepared to 50 mg/ml at pH 5.0 with 25 mM 2-[N-morpholino]ethanesulfonic acid (hereinafter "MES", manufactured by Sigma), and stirred by tipping slowly at room temperature for 30 minutes. After reaction the tube was left for 2 minutes on a neodymium magnetic, and the supernatant was removed. Finally it was washed twice with 25 mM MES at pH 5.0, for a final solution volume (40 µl).

2. Fixing of Antibodies after Activation

Rat CD44 antibodies (manufactured by Chemicon; 20 µg) were dissolved in 25 mM MES (60 µl), added to the aforementioned activated beads, and stirred by tipping slowly at room temperature for 3 hours to fix the antibodies to the activated beads. After reaction the tube was left for 2 minutes on a neodymium magnet, and the supernatant was removed. Antibodies which had not reacted with the beads were removed by adding 0.05 M ethanolamine in phosphate buffer followed by stirring by tipping slowly at room temperature for 1 hour. The fixed beads were washed for 5 minutes at 4° C. in 0.5% BSA in phosphate buffer (manufactured by Sigma). This washing operation was repeated four times. This was suspended in 0.5% BSA in phosphate buffer (1 ml) and stored at 4° C.

3. Binding of Fixed Beads to the Cell

Cultured rat myeloid mesenchymal stem cells were transferred from a dish to a tube where they were kept for 10 minutes at 4° C. An antigen-antibody reaction was performed by adding the aforementioned prepared beads (60 µl) to the cell suspension ($1 \times 10^6$ cells) followed by stirring by tipping slowly for 1 hour at 4° C. After reaction the tube was left for 2 minutes on a neodymium magnet, and the supernatant was removed. This was then re-suspended in 0.5% BSA in phosphate buffer. This washing operation was performed 4 times. Experiments were performed in suspension in phosphate buffer.

Preparation of Magnetic Cell Having Magnetic Liposome

1. Synthesis of N-[3-(2-pyridylthio)propionyl]phosphatidyl ethanolamine (hereinafter "PDP-PE")

N-Succinimidyl 3-(2-pyridylthio)propionic acid ester (25 mg) and triethylamine (50 mmol) were dissolved in anhydrous ethanol (3 ml), and phosphatidyl ethanolamine (50 mmol) was further dissolved and shaken After 5 hours, the methanol was removed under a reduced pressure, and the residue was dissolved in chloroform. A silica gel column (10 ml) which had been activated overnight at 150° C. was washed in chloroform. After washing the reaction product was run through the column and washed with further chloroform (20 ml). 20 ml each of 40:1, 30:1, 25:1, 20:1 and 15:1 mixed chloroform/methanol solutions were run through followed by 60 ml of a final 10:1 mixed solution. The 15:1 and 10:1 runs were concentrated together under a reduced pressure.

2. Preparation of Liposome

Egg phosphatidylcholine (10 mmol), cholesterol (10 mmol) and PDP-PE (1 mmol) were dissolved in diethyl ether (3 ml), and the diethyl ether was vaporized under a reduced pressure. Saline (0.9%, 1 ml) containing magnetic iron ($Fe_2O_3$, 5 mg)) and a drug to be enclosed (TGF-β, bFGF) and a boric acid/citric acid buffer (pH 6.0) were added and shaken using a vortex mixer, and the thin film adhering to the inside of the flask was completely stripped followed by 50 minutes' ultrasound treatment with a Bath Sonicator (same as above). Using a 0.45 T permanent magnet (same as above), the prepared magnetic liposomes and non-enclosed magnetic materials were isolated from the solution. After 15 minutes of centrifugation at 1000×g (rpm), the magnetic liposomes which were the supernatant were separated from the non-enclosed magnetic materials which were the sediment.

3. Binding of Liposomes with Antibodies

Human CD44 antibodies (20 µg) were dissolved in 25 mM MES (60 µl), and the prepared liposome was added and stirred by tipping slowly for 3 hours at room temperature to fix the antibodies to the liposomes. After reaction this was left for 2 minutes on a neodymium magnet, and the supernatant was removed. To remove unreacted antibodies, ethanolamine (0.05 M) in phosphate buffer was added and stirred by tipping slowly for 1 hour at room temperature.

This was washed for 5 minutes at 4° C. in 0.5% BSA phosphate buffer. This washing operation was repeated 4 times. After precipitation and stabilization with 0.5% BSA in phosphate buffer (1 ml), this was stored at 4° C.

4. Binding of Liposomes with Fixed Antibodies to the Cells

Cultured human myeloid mesenchymal stem cells were transferred from a dish to a tube, and stored for 10 minutes at 4° C. An antigen-antibody reaction was performed by adding the prepared liposomes to the cell suspension ($1\times10^6$) and stirring by tipping slowly for 1 hour at 4° C. After reaction the tube was placed for 2 minutes on a neodymium magnet, and the supernatant was removed. This was re-suspended in 0.5% BSA in phosphate buffer. This washing operation was repeated 4 times. Experiments were performed in suspension in phosphate buffer or the like.

Example 1

In Vitro Test

Myeloid mesenchymal stem cells ($4\times10^5$) bound to magnetic particles which had been prepared by the above methods were spread on a petri dish. In this example, a 4300 G round (diameter 5 mm) neodymium magnet was set under the center of the dish. In the comparative example, no magnet was used. TGF-β and dexamethasone were added to the dish. After 21 days of culture, this was evaluated by toluidine blue staining. In the example, chondroid tissue had formed locally centered on a position corresponding to the magnet. In the comparative example, chondroid tissue had not formed locally.

Figure 4:
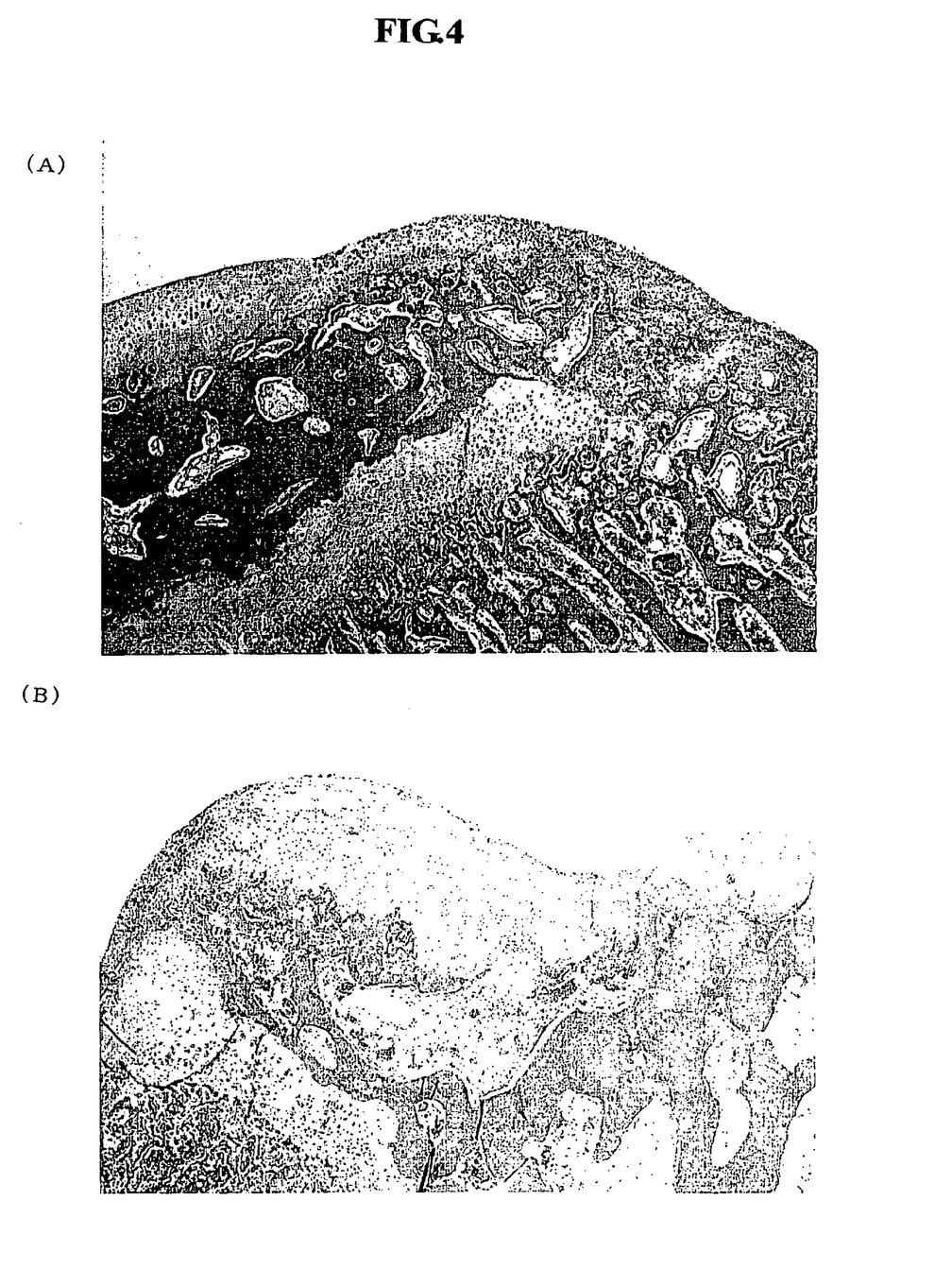
FIG. 4 shows microscopic images (50×) taken without (A) and with (B) the application of an external magnetic field for about 72 hours one month after intra-articular injection of magnetic cells according to the present invention.

FIG. 4 shows microscopic images (×50) observed 1 month after intra-articular injection of magnetic cells according to the present invention without (A) and with (B) the presence of an external magnetic field applied for about 72 hours. In FIG. 4(A), it is clear that the magnetic cells shown by black dots are observed throughout the cells. On the other hand, in FIG. 4(B), the magnetic cells shown by black dots are concentrated in the left side of FIG. 4(B). The staining in FIGS. 4(A) and (B) was actually by hematoxylin-eosine staining, and is shown in gray.

From these results, it is shown that the magnetic cells according to the present invention were moved locally by means of the action of magnets. Moreover, repair of hyalin cartilage was observed in cells which had been exposed to an external magnetic field.

Example 2

Bone Defect Repair in Rabbit Knee Joints

Bone defects 5 mm in width were introduced in two places in rabbit knee joints according to the methods described in *Bioindustry* 2002 Vol. 19 No. 6, pp. 47-53. The magnetic cells (3.0 µg) obtained in the example were administered to these defects by injection. Next, a magnet with a 700 G magnetic field was left for 9 weeks on the surface corresponding to the defects. Meanwhile, magnetic cells were administered without an external magnetic field in a comparative example. As a result, cartilage cells were locally present at the bone defects in the example and bone defect repair from bridging formation of new bone was observed, while in the comparative example without the external magnetic field no repair of bone defects was observed.

Preparation of Magnetic Cells 2

1. Activation of Magnetic Beads Using EDC and NHS 3 mg equivalent (60 µl) was taken from a ferrisphere 100C stock solution (manufactured by Japan Paint; 50 mg/ml) and washed by adding 0.01 N NaOH and agitating for 10 minutes at room temperature in a mixer. This washing operation was repeated once, and washing was performed again by adding de-ionized water and stirring at room temperature for 5 minutes in a mixer. This washing operation was repeated 3 times. To activate the magnetic beads, excess water was removed and the magnetic beads were mixed thoroughly with 50 µl each of EDC and NHS prepared to 50 mg/ml at pH 5.0 with 25 mM MES, and stirred by tipping slowly at room temperature for 30 minutes. After reaction the tube was left for 2 minutes on a neodymium magnet, and the supernatant was removed. Finally it was washed twice with 25 mM MES at pH 5.0 (final solution volume (40 µl)).

2. Fixing of Antibodies after Activation

Rat CD44 antibodies (manufactured by Chemicon) or RGDS peptides (manufactured by Peptide Laboratories) (20 µg) were dissolved in 25 mM MES (60 µl), added to the activated beads (suspended in 40 µl of 25 mM MES at pH 5.0) and stirred by tipping slowly at room temperature for 3 hours to fix the antibodies to the activated beads. After reaction the tube was left for 2 minutes on a neodymium magnet, and the supernatant was removed. To remove antibodies which had not reacted with the beads, ethanolamine (0.05 M) in PBS (−) of pH 8.0 was added, and stirred by tipping slowly at room temperature for 1 hour. The fixed beads were washed for 5 minutes at 4° C. in 0.5% BSA in PBS (−). This washing operation was repeated four times. This was suspended in 0.5% BSA (1 ml) in PBS (−) and stored at 4° C.

3. Binding of Antibody-Fixed Beads to the Cells

Cultured rat myeloid mesenchymal stem cells were transferred from a dish to a tube. An antigen-antibody reaction was accomplished by adding the prepared beads (15 µl) per 500 µl of the cell suspension ($2\times10^5$ cells) followed by stirring by tipping occasionally for 1 hour at 4° C. 0.5% BSA in PBS (−) was used as the reaction buffer here. After reaction the tube was left for 2 minutes on a neodymium magnet, and the supernatant was removed. This was then re-suspended in 0.5% BSA in PBS (−). This washing operation was performed 3-4 times. Experiments were performed in suspension in PBS (−) or the like.

Preparation of Magnetic Cells 3

1. Activation of Magnetic Beads Using EDC and NHS 3 mg equivalent (60 μl) was taken from a ferrisphere 100C stock solution (manufactured by Japan Paint; 50 mg/ml) and washed by adding 0.01 N NaOH and stirring for 10 minutes at room temperature in a mixer. This washing operation was repeated once, and washing was performed again by adding de-ionized water and stirring at room temperature for 5 minutes in a mixer. This washing operation was repeated 3 times. To activate the magnetic beads, excess water was removed and the magnetic beads were mixed thoroughly with 50 μl each of EDC and NHS prepared to 50 mg/ml at pH 5.0 with 25 mM MES, and stirred by tipping slowly at room temperature for 30 minutes. After reaction the tube was left for 2 minutes on a neodymium magnet, and the supernatant was removed. Finally it was washed twice with 25 mM MES at pH 5.0 (final solution volume (40 μl)).

2. Fixing of Antibodies after Activation

Rat CD44 antibodies (manufactured by Chemicon) or RGDS peptides (manufactured by Peptide Laboratories) (10 ng) were dissolved in 25 mM MES (60 μl) at pH 5.0, added to the activated beads (suspended in 40 μl of 25 mM MES at pH 5.0) and stirred by tipping slowly at room temperature for 3 hours to fix the antibodies to the activated beads. After reaction the tube was left for 2 minutes on a neodymium magnet, and the supernatant was removed. To remove antibodies which had not reacted with the beads, ethanolamine (0.05 M) in PBS (−) of pH 8.0 was added, and stirred by tipping slowly at room temperature for 1 hour. The fixed beads were washed for 5 minutes at 4° C. in 0.5% BSA in PBS (−). This washing operation was repeated four times. This was suspended in 0.5% BSA (1 ml) in PBS (−) and stored at 4° C.

3. Binding of Beads with Fixed Antibodies to the Cells

Cultured rat myeloid mesenchymal stem cells were removed from a dish and transferred to a tube. The prepared beads (1 μl) was added per 500 μl of the cell suspension ($2 \times 10^5$ cells) followed by stirring by tipping occasionally for 1 hour in a refrigerator (4-10° C.) in the case of the CD44 antibodies to accomplish an antigen-antibody reaction. In the case of the RGDS peptides, the reaction was accomplished by occasional tipping stir for 1 hour at 37° C. 0.5% BSA 4.4 μM EDTA in PBS (−) was used as the reaction buffer here. After reaction the tube was left for 2 minutes on a neodymium magnet, and the supernatant was removed. This was then re-suspended in 0.5% BSA in PBS (−). This washing operation was performed 3-4 times. Experiments were performed in suspension in PBS (−) or the like.

Figure 5:
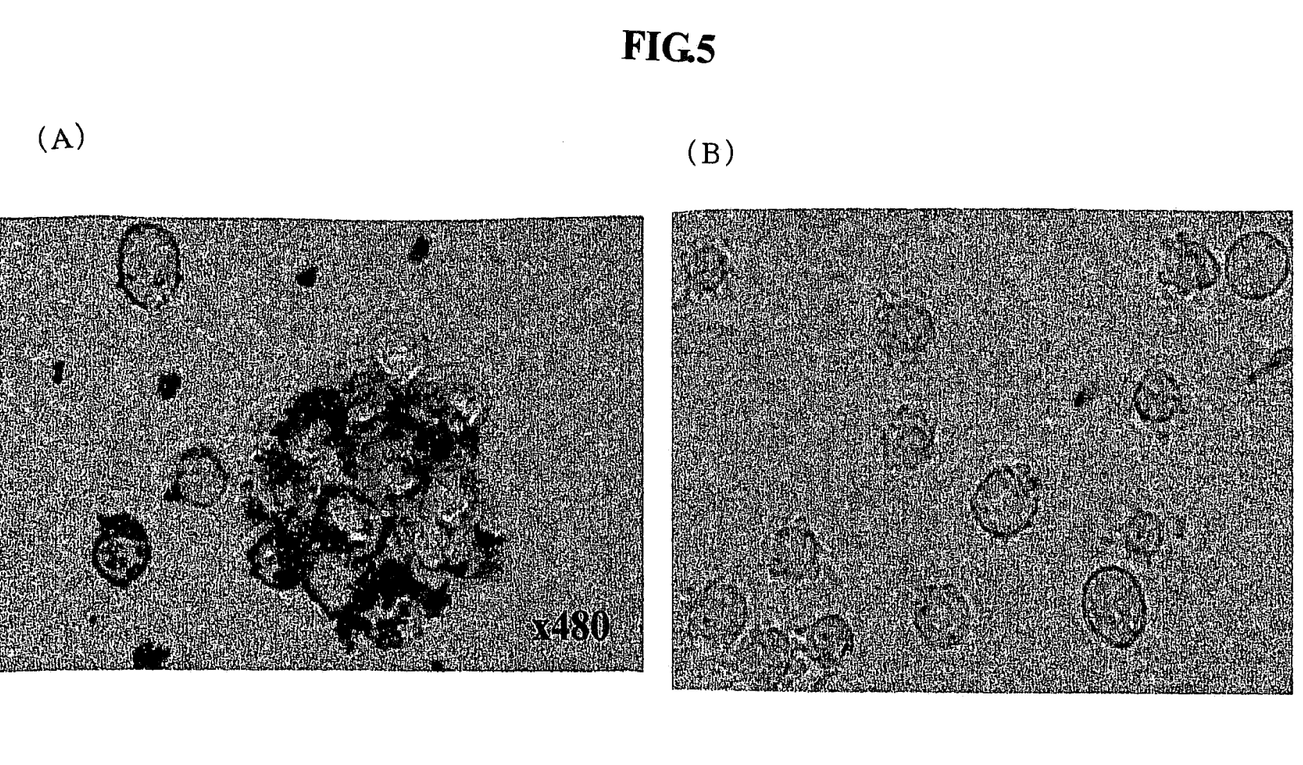
FIG. 5 shows microscopic images (480×) of magnetic cells prepared according to preparation methods 2 (5A) and 3 (5B) of the present invention in rat mesenchymal stem cells.

FIGS. 5 (A) and (B) show microscopic images (480×) of magnetic cells prepared by preparation methods 2 and 3 above, respectively, (magnetic cells mediated by integrin and RGDS peptide) as observed in rat mesenchymal stem cells. It is clear from FIG. 5 that the activity of the magnetic cells according to the present invention is affected by the amount of RGDS peptide with magnetic bodies introduced into the magnetic beads, in other words, by the amount of the aforementioned peptide coated on the magnetic beads, and ultimately the magnetic cells exhibit a greater tendency to aggregate in cells in the body the higher the aforementioned amount of introduction and the greater the quantity of magnetic beads.

Figure 6:
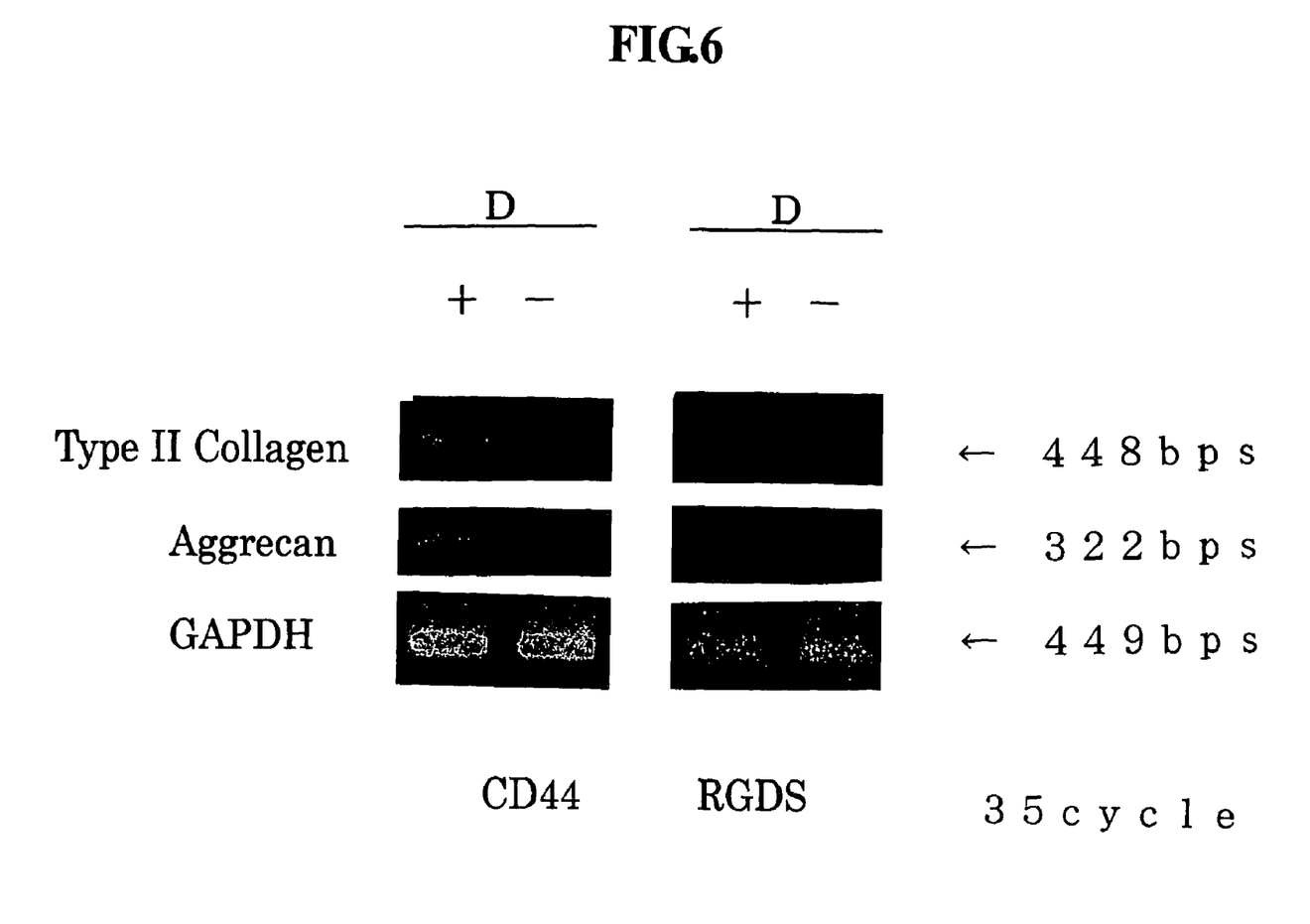
FIG. 6 shows the results for expression of Type II Collagen and Aggrecan mRNA (genes) as measured by RT-PCR after 21 days of culture when magnetic cells (rat mesenchymal stem cells) prepared with CD44 or RGDS peptide of the present invention were pellet cultured using cartilage-induction medium.

FIG. 6 shows the results for expression of Type II Collagen and Aggrecan mRNA (genes) as measured by RT-PCR after 21 days of culture when magnetic cells (rat mesenchymal stem cells) prepared with CD44 or RGDS peptide according to the present invention were pellet cultured using cartilage-induction medium. Expression of both genes was confirmed in the group (D+ group) in which differentiation was induced by addition of TGF-$\beta^3$ and dexamethasone. In the group (D− group) which was cultured without addition of TGF-$\beta^3$ and dexamethasone, on the other hand, no expression of either gene was seen. From the results shown in FIG. 6 it is supposed from Chondrogenesis of the complex-RT-PCR that magnetic cells (mesenchymal stem cells) having CD44 antigen or RGDS peptide as the linker can be induced to differentiate into cartilage cells.

Figure 7:
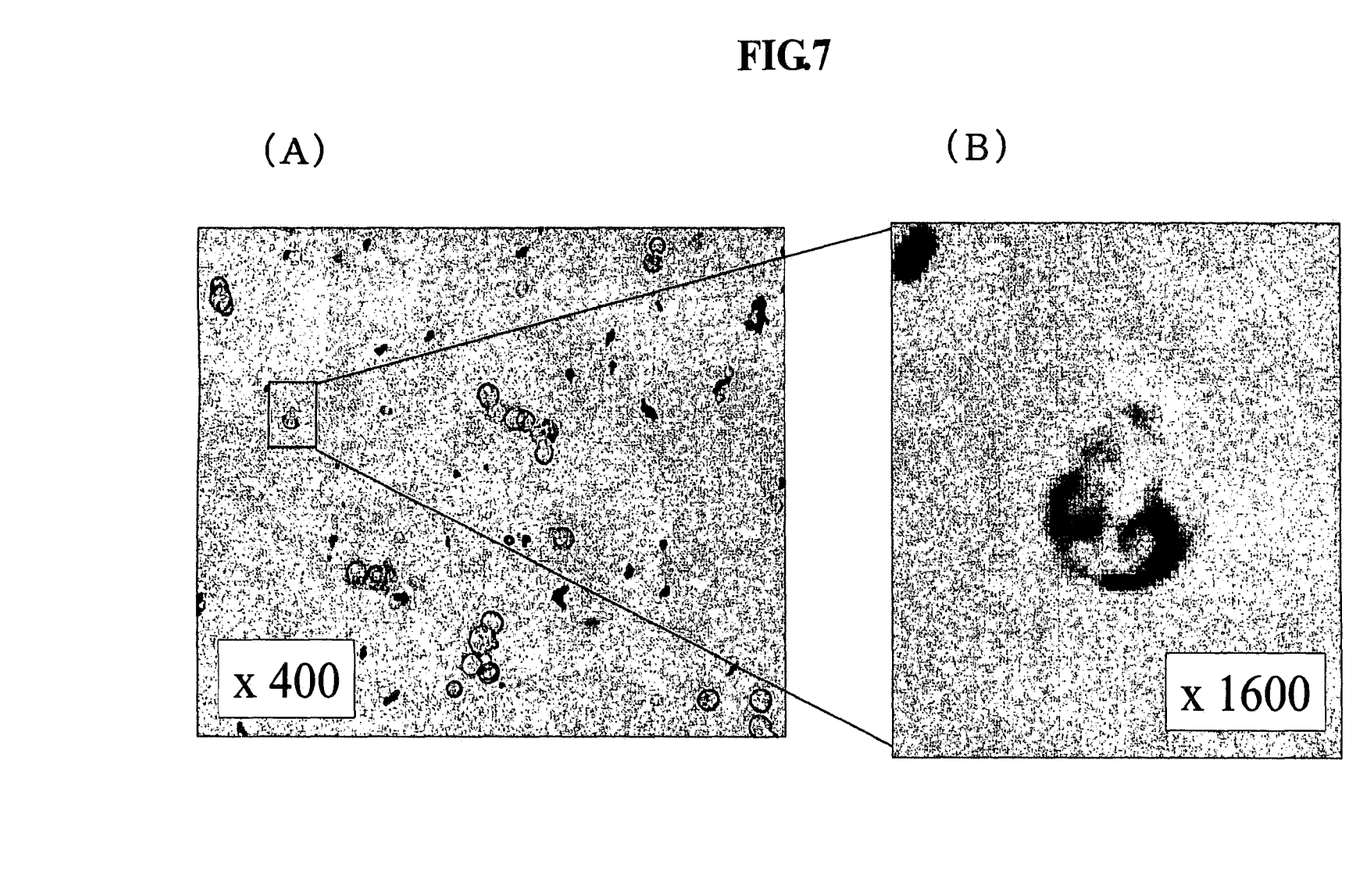
FIG. 7 shows photographs explaining magnetic cells according to the present invention formed using rat neural stem cells. (A) is a 400× image and (B) is a 1600× image.

FIG. 7 shows a photograph explaining the formation of magnetic cells according to the present invention using rat neural stem cells. From the results shown in FIG. 7, it is shown that when aggregated rat neural stem cells were scattered by pipette and beads modified with the aforementioned RGDS peptide were then applied, magnetic cells using rat neural stem cells were formed via the integrin of the neural stem cells.

The invention claimed is:

1. A combination comprising:
   a magnet; and
   a magnetic cell comprising:
   a cell having integrin on the surface thereof; and
   a magnetic particle comprising a peptide having an adhesive activity for integrin and a magnetic material,
   wherein the magnetic particle is coated with the peptide at a ratio of from 3 ng to 6.6 μg of the peptide to 1 mg of the magnetic particle.

2. The combination according to claim 1, wherein the cell is selected from the group consisting of:
   a cultured chondrocyte, a mesenchymal cell, a lymphocyte, and a neural stem cell.

3. The combination according to claim 1, wherein the magnetic cell further comprises a drug.

4. The combination of any one of claims 1-3, wherein the peptide has an amino acid sequence comprising RGDS or GRGDS.

5. A method for forming a chondroid tissue from a myeloid mesenchymal stem cell, comprising the steps of:
   providing a magnetic cell comprising:
   the myeloid mesenchymal stem cell;
   an adhesive molecule present on the cell surface;
   a linker bound to the adhesive molecule by an antigen-antibody using a CD44 antibody; and
   a magnetic particle which comprises at least magnetic material and TGF-β, and which is bound by the linker; and
   culturing the magnetic cell using a magnet.

6. The method of claim 5, wherein the cultured magnetic cell is administered in vivo.

* * * * *